(12) United States Patent
Boudjemline (10) Patent No.: US 7,273,489 B2
(45) Date of Patent: Sep. 25, 2007

(54) DEVICE FOR OCCLUDING A HOLE IN A BODY WALL AND A UNIT FOR INSERTING SAID DEVICE

(76) Inventor: Younes Boudjemline, 8 Passage de la Vallee, Clamart (FR) 92140

( * ) Notice: Subject to any disclaimer, the term of this patent is extended or adjusted under 35 U.S.C. 154(b) by 104 days.

(21) Appl. No.: 10/522,898

(22) PCT Filed: Jul. 28, 2003

(86) PCT No.: PCT/FR03/02386

§ 371 (c)(1),
(2), (4) Date: Feb. 1, 2005

(87) PCT Pub. No.: WO2004/012572

PCT Pub. Date: Feb. 12, 2004

(65) Prior Publication Data

US 2005/0245964 A1    Nov. 3, 2005

(30) Foreign Application Priority Data

Aug. 1, 2002  (FR) .................................. 02 09807

(51) Int. Cl.
*A61B 17/03* (2006.01)
*A61B 17/122* (2006.01)
(52) U.S. Cl. .................... 606/213; 606/151; 604/272
(58) Field of Classification Search .............. None
See application file for complete search history.

(56) References Cited

U.S. PATENT DOCUMENTS

| | | | | |
|---|---|---|---|---|
| 5,116,357 A | * | 5/1992 | Eberbach | 606/213 |
| 5,171,259 A | * | 12/1992 | Inoue | 606/213 |
| 5,258,000 A | * | 11/1993 | Gianturco | 606/151 |
| 5,391,182 A | * | 2/1995 | Chin | 606/213 |
| 5,397,331 A | * | 3/1995 | Himpens et al. | 606/151 |
| 6,248,116 B1 | | 6/2001 | Chevillon et al. | |
| 6,342,059 B1 | | 1/2002 | Chevillon et al. | |
| 6,355,052 B1 | * | 3/2002 | Neuss et al. | 606/213 |
| 6,375,671 B1 | | 4/2002 | Kobayashi et al. | |
| 6,626,919 B1 | | 9/2003 | Swanstrom | |
| 6,669,707 B1 | | 12/2003 | Swanstrom et al. | |
| 2001/0010005 A1 | * | 7/2001 | Kammerer et al. | 606/151 |
| 2002/0065524 A1 | | 5/2002 | Miller et al. | |

* cited by examiner

*Primary Examiner*—Glenn K. Dawson
(74) *Attorney, Agent, or Firm*—Young & Thompson (57) ABSTRACT

The device includes a solid disk (1) whose diameter is larger than the diameter of a hole (2) to be treated and which is formed by a peripheral deformable thread (6) made of a shape memory material and a flexible membrane (6) which is made of biocompatible material and connected to the thread; and at least an attachment (15) separated from the disk (1) which makes it possible to fix the disk (1) to the body wall. Each attachment (15) is provided with an area (16) for linking to the disk and an area (16) for linking to the body wall (3) and is embodied such that it is deformable and can be introduced into a hollow needle (28).

14 Claims, 5 Drawing Sheets

DEVICE FOR OCCLUDING A HOLE IN A BODY WALL AND A UNIT FOR INSERTING SAID DEVICE

BACKGROUND OF THE INVENTION

This invention relates to a device for occluding a hole existing in a body wall, insertable by mini-invasive non chirurgical route, i.e. going through body ducts. The invention also relates to a unit for inserting said device.

The invention is applicable in particular to the occlusion of septal defects between the right-hand auricle and the left-hand auricle or between the right-hand ventricle and the left-hand ventricle of a heart.

Closing such septal defects is performed usually by surgical intervention or by using a cardiac catheter running through the vessels, wherein deployable occlusion devices are placed.

The document U.S. Pat. No. 5,846,261 A describes one of these devices, composed of two voluminous and rigid disks, wider than the communication to be closed, and of an inter-disk portion of the size of the communication to be sealed. The implantation is visualised thanks to X-rays on a two-dimensional imaging screen. The device is loaded in the catheter, then is brought forward into the left-hand auricle through the interauricular communication; the first disk is then extracted from the catheter and is applied to the interauricular septum, thereby occluding the communication; the second disk is then extracted from the catheter and sandwiches the interauricular septum closing the communication.

Although simple, the use of such devices is limited to the treatment of holes or of communications present in tissular walls with a certain bank width, equal to or greater than 7 millimetres, and not exceeding a certain size. Moreover, the rigidity of the device described by the previous document makes it unusable in young children.

There results that numerous interauricular communications are closed by surgical route, with direct control of the communication to be treated. This surgery involves opening the thorax and implementing extracorporeal circulation to empty the blood from the heart and enable stitching up the septal defect. In case of large size communication, a pericardium or PTFE patch is necessary for the occlusion.

The document EP 1,046,375 A1 describes a similar device, with two disks connected together. These disks have a diameter slightly greater than the diameter of the communication to be treated and are connected by an elastic thread, which thread enabling, after implantation, to maintain the disks pressed against the respective faces of the body wall treated.

The purpose of the present invention is to provide a device which is easier to insert than that according to this previous document, with smaller space requirements, and held more securely onto said body wall.

The document WO 01/30267 describes devices for closing or excluding a cavity, comprising an occlusion disk and a structure for anchoring said disk to the body walls forming said cavity.

The device according to this document is not suited to the occlusion of a hole or communication existing in a body wall, in particular in the interauricular septum of a heart, by very little invasive route.

OBJECTS OF THE INVENTION

The purpose of the present invention is to provide a device for occluding a hole or communication existing in a body wall, while remedying the shortcomings of the existing devices. The purpose of the invention is in particular to provide a device with small space requirements, whereof the implantation is very little invasive and which is attached to a body wall treated in a very reliable fashion.

SUMMARY OF THE INVENTION

According to the invention, the device comprises:
a single disk, of diameter greater than the diameter of the hole to be treated, composed of a deformable peripheral thread made of shape memory material, and of a flexible wall made of a biocompatible material connected to said thread, whereas said disk is deformable between a normal deployment state, wherein it may be pressed against said body wall and brought to cover the complete hole to be treated, while extending over said hole, and a contraction state, wherein it may be inserted into a sheath enabling to run it towards said body wall for being inserted therein, whereas the disk comprises moreover means for removable link thereof with a handling rod, enabling to insert said disk and to maintain it pressed against said body wall; and
at least one attachment separated from the disk, enabling to fasten said disk to said body wall, whereas each attachment comprises a zone for linking to the disk and a zone for linking to the body wall and which may be deformed in order to engage into a hollow needle.

The unit for inserting the device comprises:
said sheath, liable to receive the disk in said contraction state of this disk and to contain said handling rod;
at least one catheter containing said hollow needle, this needle being made of a shape memory material and deformable between a substantially linear shape, which it adopts when inserted into the catheter, and a shape wherein its free end portion is offset laterally relative to its other end portion, a shape which it adopts when pushed outside the catheter, such offset being such that it enables said free end portion to face the zone of said body wall covered with said flexible wall of the disk and to go through said zone when the needle is pushed outside the catheter; and
a control rod, engaged into the catheter and connected removably to said attachment, enabling to control the sliding of this attachment through said needle.

The disk, connected to the handling rod, may thus be routed towards the body wall to be treated using said sheath, then be deployed by retraction of said sheath and be pressed against the body wall by means of the handling rod. The hollow needle is then pushed outside the catheter containing said needle in order to offset the free end portion thereof, then to insert it through said zone of the body wall covered by the flexible wall of the disk. The attachment is then pushed through the needle by dint of said control rod in order to engage its linking zones with the disk and the body wall, respectively.

One or several attachments are inserted, then the control and handling rods are removed.

This unit according to the invention enables to insert the device in a very little invasive fashion, while avoiding to resort to appended imaging devices and especially by enabling to master perfectly the positioning of the needle(s) with respect to the disk and therefore relative to the communication to close, said positioning being determined by the shape of the needle(s) in deployed state.

Attachments may be placed on the whole periphery of the disk, in order to hold said disk against the body wall and to provide permanent occlusion of the hole contained in said wall, or one or several attachments may be inserted on a marginal sector of this periphery, so that the disk does not occlude permanently the hole to be treated and may operate like a flap. This second implantation mode may prove extremely interesting for patients with pulmonary arterial hypertension.

The means for removable link of the disk to the handling rod may comprise a radial thread interconnected with said peripheral thread of the disk, including at the centre of the disk, a tapped socket, whereby said handling rod contains a threaded end which may be screwed into said socket.

The flexible wall of the disk may be of PTFE (polytetrafluoroethylene) or of pericardium, and the peripheral thread may be of nickel-titanium alloy, known under the designation 'nitinol'.

Said linking zones, included in each attachment, may be in the form of two distant deployable bearing surfaces, separated from one another by a tapered intermediate portion of length corresponding substantially to the added thickness of said body wall and of said flexible wall of the disk, whereas one of said bearing surfaces of the attachment is intended for resting against said flexible wall of the disk and the other bearing surface of this attachment is intended for resting against said body wall, on the side of this wall opposite the disk, said tapered intermediate portion being intended for running through said body wall.

When inserting an attachment, after the needle has been engaged through the body wall and through the disk, the attachment is pushed in order to extract one of its bearing surfaces outside the needle and to deploy this surface, then the needle is retracted in order to extract said tapered intermediate portion and the other bearing surface from the attachment so that said other bearing surface rests against the body wall on the side opposite that against which the disk rests.

The bearing surfaces included in the attachment may be in the form of spirals formed by a thread making up the attachment, or in the form of branches or radial wings.

This attachment may also be of nickel-titanium alloy, known under the designation 'nitinol'.

The catheter may be interconnected with the handling rod, or may slide along said rod. In the second case, the handling rod comprises a stop enabling axial positioning of the catheter relative to the disk in order to offset suitably said free end portion of the needle.

In either case, the axial position adopted by the catheter relative to the handling rod, hence with respect to the disk, when deploying the needle, is determined accurately, either by linking said catheter to the handling rod, or by said stop. This position has been determined in function of the shape of the needle in deployed state, and enables perfect control of the position of the needle relative to the disk and hence relative to the communication to be closed.

The sliding assembly of the catheter relative to the handling rod advantageously reduces the size of the vascular access necessary, whereas each element of the occlusion device is brought to the implantation site one after the other.

The catheter may also be mounted to pivot around the handling rod. The same catheter may then be used for inserting several attachments at different locations of the periphery of the disk, by pivoting the catheter around the handling rod.

The catheter and the handling rod may then comprise respectively a mark and a graduation enabling to position the catheter angularly relative to the handling rod.

The unit according to the invention may also comprise several catheters arranged angularly according to the different implantations of the attachments to be realised.

The needle may also be of nickel-titanium alloy, known under the designation 'nitinol'.

The means for removable linking of the control rod to the attachment may also be in the form of a tapped socket and of a threaded end which may be screwed into said socket.

The invention will be better understood, and other characteristics and advantages thereof will appear, with reference to the appended schematic drawing, representing, for non-limiting exemplification purposes, several possible embodiments of the device related and of a unit for inserting said device.

DESCRIPTION OF THE PREFERED EMBODIMENT

Figure 1:
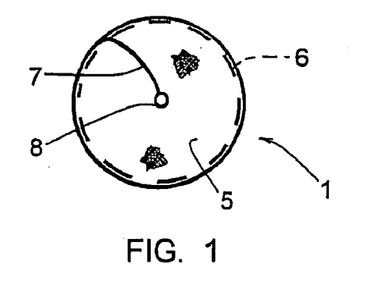
FIGS. 1 and 2 are views, respectively planar and lateral views, of a disk included in said device.
Figure 2:
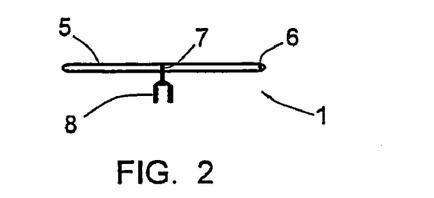
Figure 15:
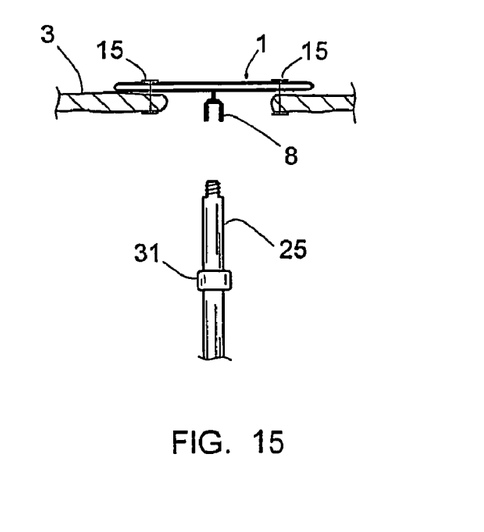

FIGS. 1 and 2 represent a disk 1 enabling, as shown on FIG. 15, to occlude a hole or communication 2 included in a body wall 3, i.e. the interauricular septum of a heart.

The disk 1 includes a flexible wall 5 of PTFE (polytetrafluoroethylene) connected to a peripheral thread 6 of nickel-titanium alloy, known under the designation 'nitinol', and a radial thread 7 comprising, in the centre of the disk 1, a tapped socket 8, oriented axially.

The disk 1 exhibits a diameter greater than the diameter of the hole 2 to be treated.

Figure 9:
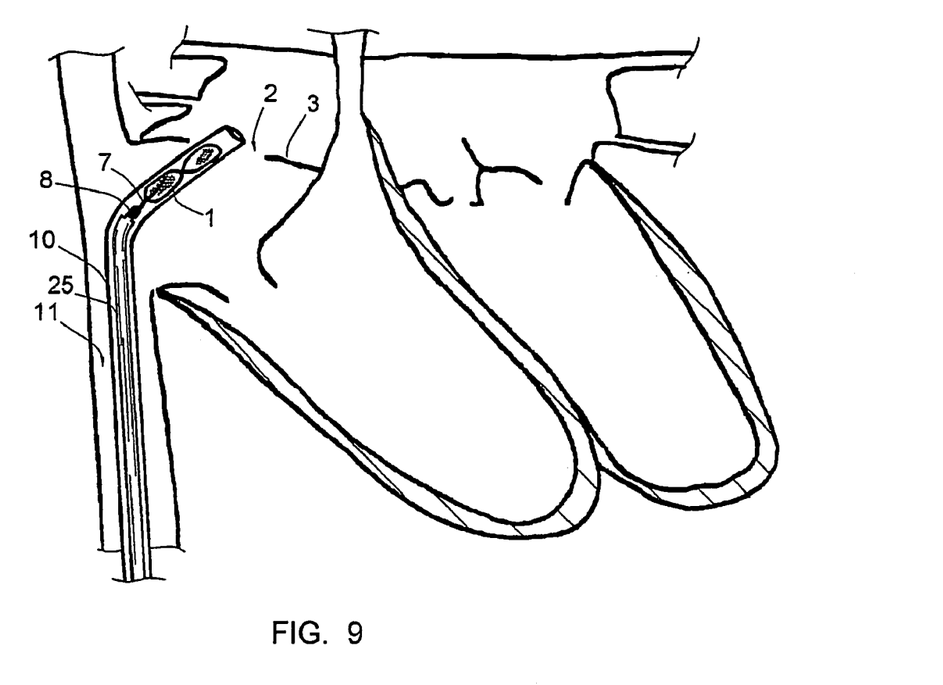
FIGS. 9 to 15 are views of different successive steps of the insertion of the device on a right-hand auricle of a heart.
Figure 10:
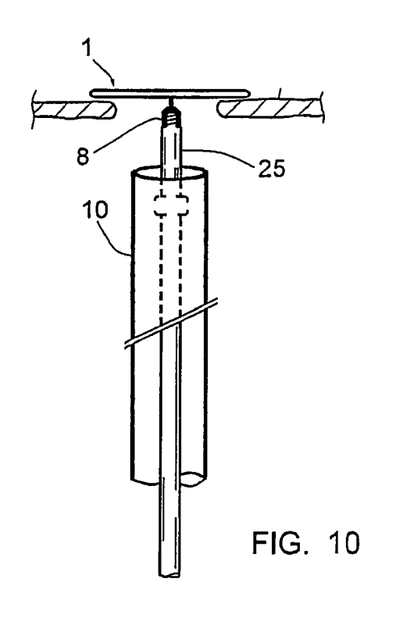
Figure 11:
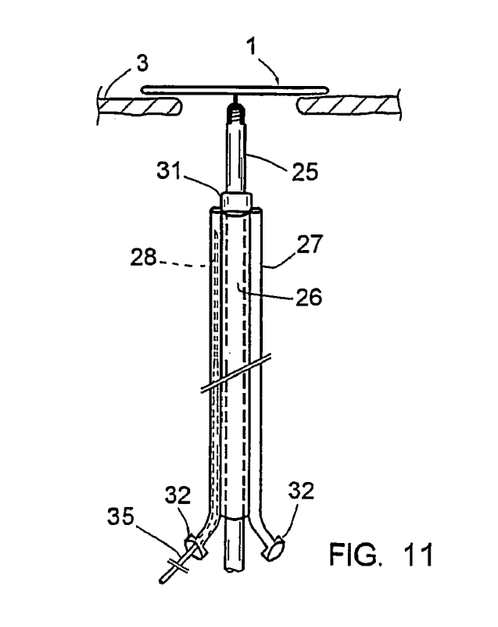

The disk 1 may be deformed to be engaged into a sheath 10 for routing to the site of implantation, while following a vascular duct 11, as shown on FIG. 9.

Figure 3A:
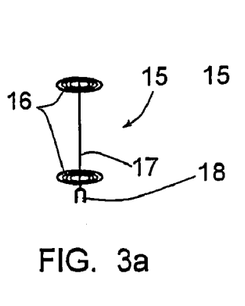
FIGS. 3a to 3c are perspective views of three embodiments of an attachment included in the device.
Figure 3B:
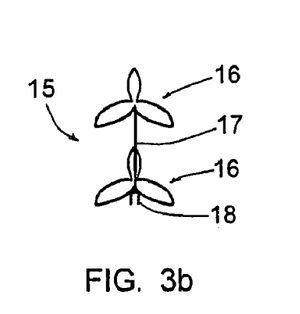
Figure 3C:
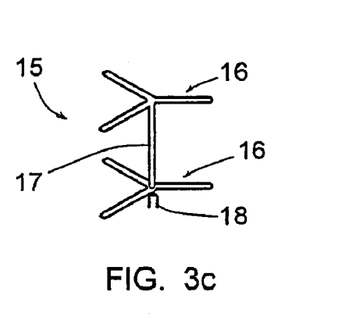

The disk 1 is fastened to the body wall 3 by means of attachments 15, more particularly visible on FIGS. 3a to 3c.

Each attachment 15 comprises two distant deployable bearing surfaces 16, separated from one another by a tapered intermediate portion 17 of length corresponding substantially to the added thickness of the body wall 3 and of the wall 5 of the disk 1.

Each attachment 15 is made of 'nitinol' and may be deformed in order to be engaged into a hollow needle 28 described below.

In the case of the attachment 15 shown on FIG. 3a, the bearing surfaces 16 are in the form of spirals made by a thread constituting the attachment; in the case of the attachments shown by FIGS. 3b and 3c, the bearing surfaces 16 are in the form of branches or radial wings arranged 120° relative to one another.

Figure 13:
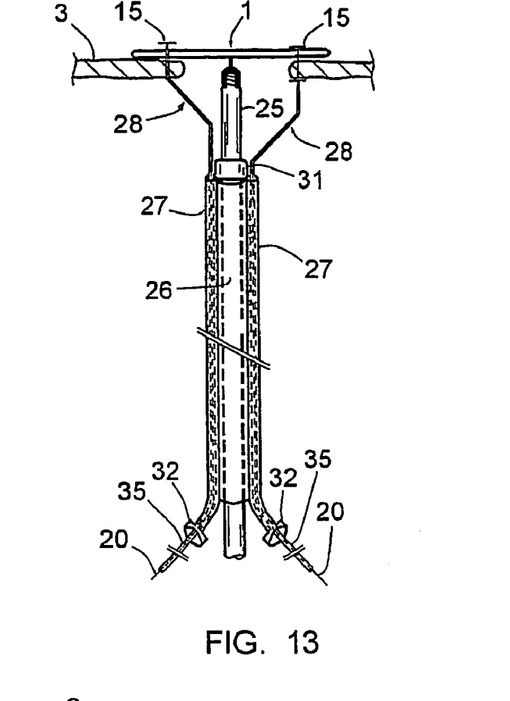
Figure 14:
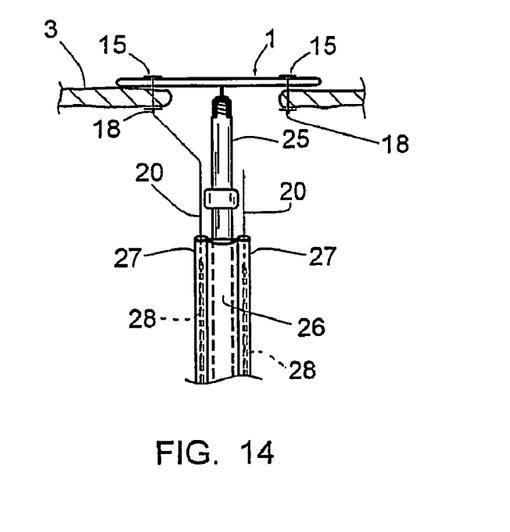

Each attachment 15 comprises moreover a tapped socket 18 which enables the removable link thereof to a control rod 20, visible on FIGS. 13 and 14, the latter comprising a corresponding threaded end.

Figure 4:
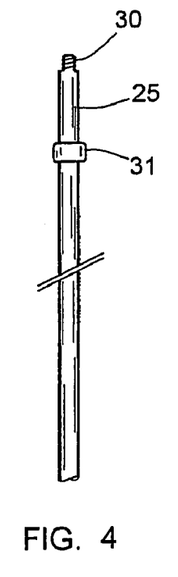
FIG. 4 is a side view of a handling rod included in said unit.
Figure 5A:
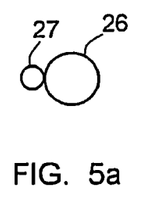
FIGS. 5a to 5e and 6a to 6e are views, respectively end and side views, of different variations of a guiding sheath and of catheters included in said unit.
Figure 5B:
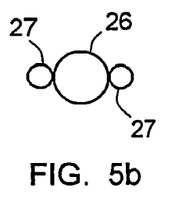
Figure 5C:
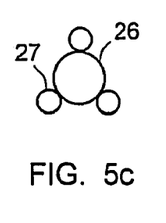
Figure 5D:
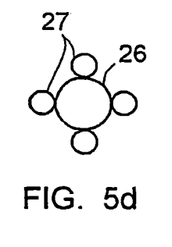
Figure 5E:
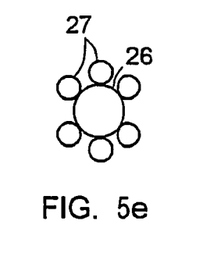
Figure 6A:
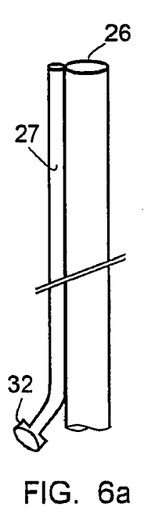
Figure 6B:
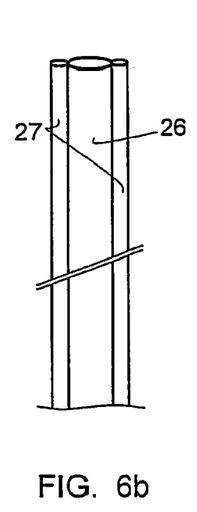
Figures 6C, 6D:
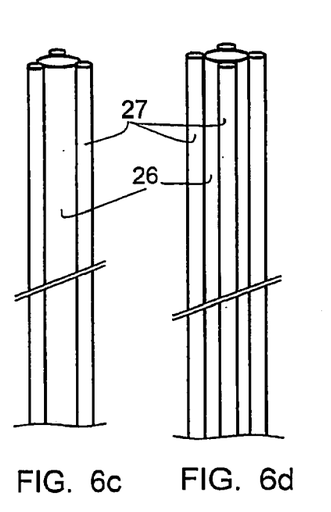
Figure 6E:
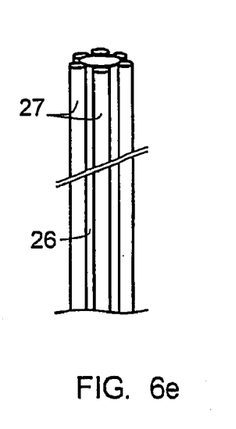
Figure 7:
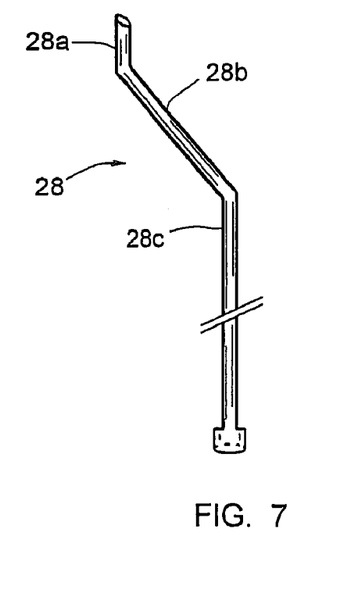
FIG. 7 is a side view of a hollow needle included in said unit.

The implantation of the disk 1 is performed using a unit including, in addition to the sheath 10 aforementioned, the handling rod 25 shown on FIG. 4, the guiding sheath 26 and the catheter(s) 27 shown on FIGS. 5a to 6e, and one or several needles 28, whereof the one is shown on FIG. 7.

These rod 25, sheath 26 and catheters 27 exhibit lengths such that they may be handled from the outside of the patient's body when the disk 1 lies by the wall 3, and have flexibilities enabling them to go past the bends which may be formed by the vascular duct 11 used for the introduction thereof.

The handling rod 25 comprises a threaded end 30 which may be screwed into the socket 8 and thereby ensure removable link of the disk 1 thereto, and includes a stop 31 interconnected thereto, situated in a precise location, explained below.

The guiding sheath 26 has such a diameter that it may be engaged slidingly on the rod 25 until it abuts against the stop 31. It may include one to six catheters 27, the latter being spaced regularly over its periphery.

Each catheter 27 is connected to the sheath 26 and may receive slidingly a needle 28. Each catheter 27 has a proximal insert 32 enabling connection to an injection syringe of an appropriate liquid, so that its lumen may be purged to avoid embolisms.

Figure 12:
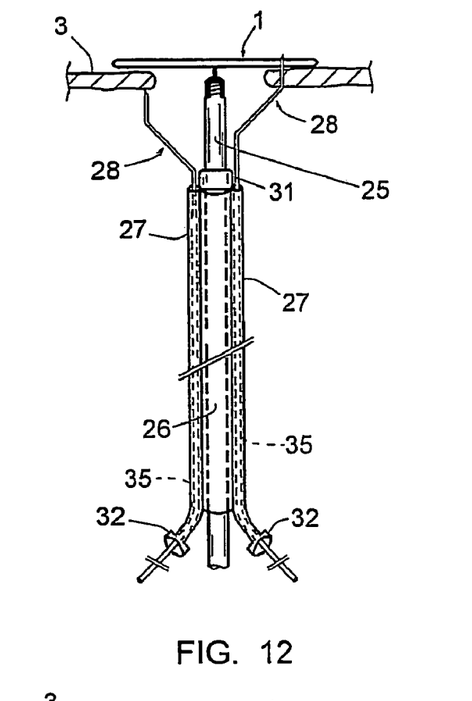

Each needle 28 is made of nickel-titanium alloy, known under the designation 'nitinol', and is deformable between a substantially rectilinear shape, which it takes on when inserted into the catheter 27, and the deflected shape shown on FIG. 7, which it takes on when pushed outside the catheter 27. In this deflected shape, it has a double bend, dividing it into a free end portion 28a, an oblique intermediate portion 28b and its other end portion 28c, said free end portion 28a being offset laterally relative to this other end portion 28c. This offset is such that it enables said free end portion 28a to face the zone of the body wall 3 covered with the wall 5 of the disk 1 and to go through this zone when the needle 28 is pushed further outside the catheter 27, as shown on FIGS. 12 and 13.

Figure 8:
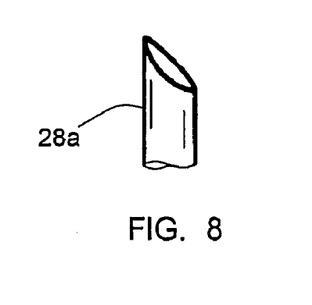
FIG. 8 is an enlarged view of the free end of this needle.

The needle 28 is bevelled at its free end, as shown on FIG. 8, for easier penetration thereof through the walls 3 and 5, and is connected by its other end to a catheter 35 emerging outside the patient, whereas said catheter may receive slidingly an attachment 15 connected to a control rod 20.

In practice, as shown on FIGS. 9 to 15, the disk 1 connected to the rod 25 is routed towards the wall 3, whereas this disk and this rod are contained inside the sheath 10, which sheath maintains the disk in contracted state (FIG. 9), until it traverses the hole 2; the sheath 10 is then removed to enable deployment of the disk 1 (FIG. 10), then the guiding sheath 26 is engaged on the rod 25 until it abuts against the stop 31, and the needles 28 and catheter 35 are engaged into the catheters 27 (FIG. 11); the needles 28 are then pushed partially outside the catheters 27 to provide the offset aforementioned of their free ends 28a (left-hand needle on FIG. 12), then the insertion thereof through the wall 3 and 5 (right-hand needle on FIG. 12), and the attachments 15, connected to the rods 20, are introduced and slid in the catheters 35 then into the needles 28, until they emerge outside these needles 28, which enables deployment of the distal bearing surfaces 16 (left-hand needle on FIG. 13); the needles 28 are then retracted in order to free the portions 17 and the other bearing surfaces 16 of the attachments 15, fastening the disk 1 to the wall 3 (right-hand needle on FIG. 13); the rods are then detached from the attachments 15 (FIG. 14), then the rod 15 is detached from the disk 1 (FIG. 15).

Figure 16A:
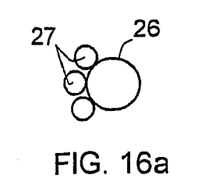
FIGS. 16a and 16b are end views of two variations of another guiding sheath and of catheters included in said unit.
Figure 16B:
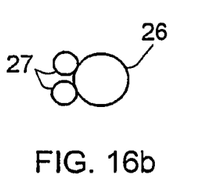
Figure 17:
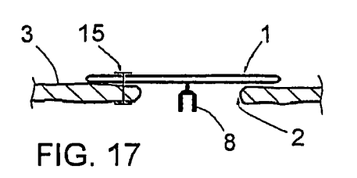
FIGS. 17 and 18 are side views of a disk included in the device, after implantation by means of the sheath and of catheters according to one of FIGS. 16a or 16b, in two operating positions.
Figure 18:
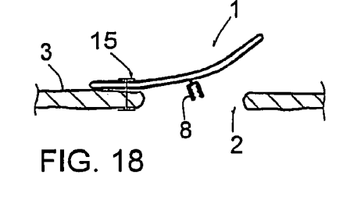

FIGS. 16a and 16b show that the sheath 26 may only comprise catheters 27 on a marginal sector of its periphery; attachments 15 may be placed using the assembly including such a sheath and such catheters that on a corresponding marginal sector of the disk 1, so that this disk 1 does not occlude permanently the hole 2 to be treated and may operate like a flap, as shown on FIGS. 17 and 18. This second implantation mode may be extremely interesting in patients having a pulmonary arterial hypertension.

The invention thus provides a device for occluding a hole existing in a body wall, which may be inserted by a very little invasive route, i.e. running through body ducts, and exhibiting the decisive advantages of having small space requirements, of being relatively easy to implant and held securely to said body wall. The invention also supplies a unit for inserting this device, enabling insertion of the device in a very little invasive fashion, without resorting to appended imaging instruments, and especially by controlling perfectly the positioning of the needle(s) relative to the disk and therefore the communication to be sealed.

It goes without saying that the invention is not limited to the embodiment described above by way of illustration, but extends to all embodiments covered by the appended claims.

In particular, the catheter(s) 27 may be interconnected with the handling rod 25, whereas the axial position of this(these) catheter(s) relative to this rod is then determined by linking this(these) catheter(s) to this rod, instead of the stop 31.

The catheter 26 may also be mounted to pivot around the handling rod 25. The same catheter 27 may then be used for inserting several attachments 15 at different locations of the periphery of the disk 1, by pivoting the catheter 26 around the handling rod 25.

Figure 19:
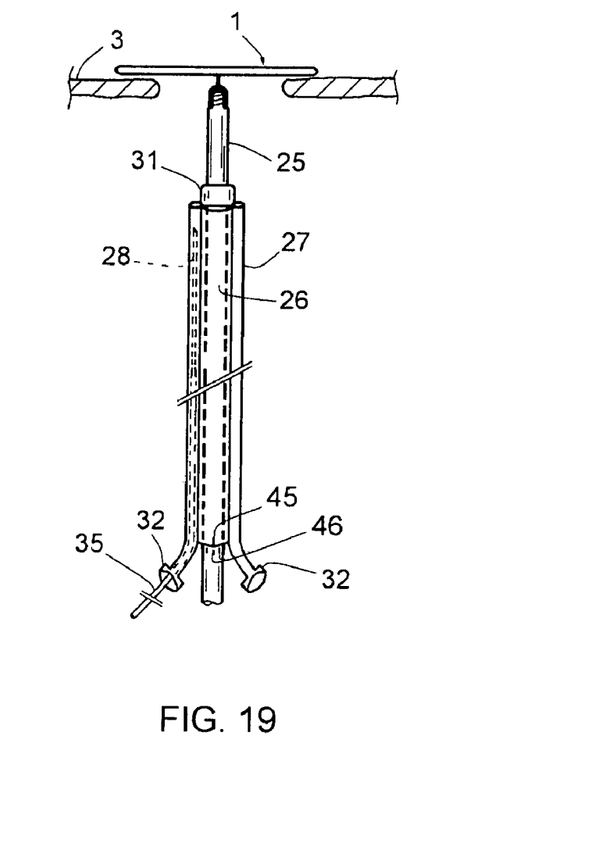
FIG. 19 is a lateral view of the device having a mark and a graduation.

The catheter 26 and the handling rod 25 may then comprise respectively, as shown on FIG. 19, a mark 45 and a graduation 46 enabling to position the catheter 26 angularly relative to the handlinq rod 25.

Figure 20:
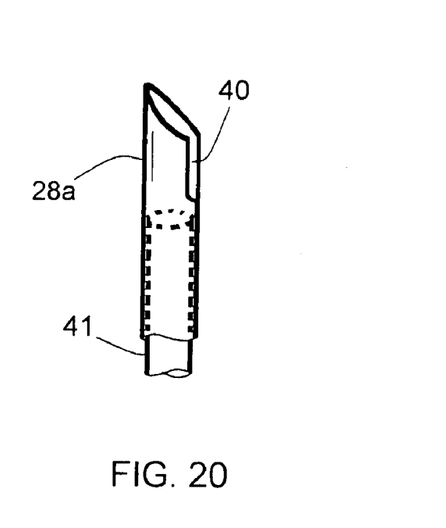
FIG. 20 is an enlarged view of the free end of said needle according to another embodiment.

The needle 28 can have an opening at its distal end, as shown on FIGS. 7 and 8, or may include a lateral slot 40 at its distal end 28a, as shown on FIG. 20, and be fitted with a removable means for occluding said slot. This removable means may notably be a flexible tube 41 sliding inside the needle. The attachment 15 is then deployed through said lateral slot 40, whereas the latter may be exposed by retracting the sliding tube 41.

The distal end of the needle may, in such a case, be full, forming a cul-de-sac.

The attachment may exhibit, notably for use with a needle including such a lateral slot 40, the form of a clamp, i.e. include two end branches, forming said linking zones, and an intermediate branch, whereas said end branches adopt, in deployed state of the attachment, a position perpendicular to the intermediate branch.

What is claimed is:

1. A unit for inserting by a mini-invasive route a device for occluding a hole existing in a body wall, characterized in that it comprises:
    a single disk, of diameter greater than the diameter of the hole to be treated, composed of a deformable peripheral thread made of shape memory material, and of a flexible wall made of a biocompatible material connected to said thread, whereas said disk is deformable between a normal deployment state, wherein it may be pressed against said body wall and brought to cover the complete hole to be treated, while extending over said hole, and a contraction state, wherein it may be inserted into a sheath enabling to run it towards said body wall for being inserted therein, whereas the disk comprises means for removable linking thereof with a handling rod, enabling to insert said disk and to maintain it pressed against said body wall;
    said handling rod;
    at least one attachment separated from the disk, enabling to fasten said disk to said body wall, whereas each attachment comprises a zone for linking to the disk and a zone for linking to the body wall and which may be deformed in order to engage into a hollow needle;
    said sheath, liable to receive the disk in said contraction state of this disk and to contain said handling rod;
    said hollow needle;
    at least one catheter containing said hollow needle, this needle being made of a shape memory material and deformable between a substantially linear shape, which it adopts when inserted into the catheter, and a shape wherein its free end portion is offset laterally relative to its other end portion, a shape which it adopts when pushed outside the catheter, such offset being such that it enables said free end portion to face the zone of said body wall covered with said flexible wall of the disk and to go through said zone when the needle is pushed outside the catheter; and
    a control rod, engaged into the catheter and removably connected to said attachment, enabling to control the sliding of this attachment through said needle.

2. The unit according to claim 1, characterized in that the means for removable link of the disk to said handling rod comprise a radial thread interconnected with said peripheral thread of the disk, including at the centre of the disk, a tapped socket, whereby said handling rod contains a threaded end which may be screwed into said socket.

3. The unit according to claim 1, characterized in that said linking zones included in each attachment are in the form of two distant deployable bearing surfaces, separated from one another by a tapered intermediate portion of length corresponding substantially to the added thickness of said body wall and of said flexible wall of the disk; whereas one of said bearing surfaces of the attachment is intended for resting against said flexible wall of the disk and the other bearing surface of this attachment is intended for resting against said body wall, on the side of this wall opposite the disk, said tapered intermediate portion being intended for running through said body wall.

4. The unit according to claim 3, characterized in that the bearing surfaces are in the form of spirals formed by a thread making up the attachment, or in the form of branches or radial wings.

5. The unit according to claim 1, characterized in that the catheter may slide along said handling rod and in that the handling rod comprises a stop enabling axial positioning of the catheter relative to the disk in order to offset suitably said free end portion of the needle.

6. The unit according to claim 1, characterized in that the catheter is mounted to pivot around the handling rod.

7. The unit according to claim 6, characterized in that the catheter and the handling rod comprise respectively a mark and a graduation enabling to position the catheter angularly relative to the handling rod.

8. The unit according to claim 1, characterized in that it comprises several catheters arranged angularly according to the different implantations of the attachments to be provided.

9. The unit according to claim 1, characterized in that the means for removable linking of the control rod and of the attachment are in the form of a tapped socket and of a threaded end which may be screwed into said socket.

10. The unit according to claim 1, characterized in that the needle includes a lateral slot at its distal end and is fitted with a removable means for occluding said slot, notably in the form of a flexible tube sliding inside the needle.

11. The unit according to claim 10, characterized in that the distal end of the needle is full, forming a cul-de-sac.

12. A surgical process for mini-invasive occlusion of a hole existing in a body wall comprising the following steps:
    using a single disk, of diameter greater than the diameter of the hole to be treated, composed of a deformable peripheral thread made of shape memory material, and of a flexible wall made of a biocompatible material connected to said thread, whereas said disk is deformable between a normal deployment state, wherein it may be pressed against said body wall and brought to cover the complete hole to be treated, and a contraction state, wherein it may be inserted into a sheath enabling to run it towards said body wall for being inserted therein, whereas the disk comprises means for removable linking thereof with a handling rod, enabling to insert said disk and to maintain it pressed against said body wall; and
    using at least one attachment separated from the disk, enabling to fasten said disk to said body wall, whereas each attachment comprises two distant deployable bearing surfaces, separated from one another by a tapered intermediate portion of length corresponding substantially to the added thickness of said body wall and of said flexible wall of the disk, the attachment being liable to be deformed to be engaged into a hollow needle; whereas one of said bearing surfaces of the attachment is intended for resting against said flexible wall of the disk and the other bearing surface of this attachment is intended for resting against said body wall, on the side of this wall opposite the disk, said tapered intermediate portion being intended for running through said body wall;
    using a unit for inserting the device including: (i) said sheath, liable to receive the disk in said contraction state of this disk and to contain said handling rod; (ii) at least one catheter containing said hollow needle, this needle being made of a shape memory material and deformable between a substantially linear shape, which it adopts when inserted into the catheter, and a shape wherein its free end portion is offset laterally relative to its other end portion, a shape which it adopts when pushed outside the catheter, this offset being such that it enables said free end portion to face the zone of said body wall covered with said flexible wall of the disk and to go through said zone when the needle is pushed outside the catheter; and (iii) a control rod, engaged into the catheter and connected removably to said attachment, enabling to control the sliding of this attachment through said needle;

routing the disk, connected to the handling rod, towards the body wall to be treated using said sheath, then deploying this disk by retraction of said sheath and pressing the disk against the body wall by means of the handling rod;

pushing the hollow needle outside the catheter containing said needle in order to offset the free end portion thereof, then inserting it through said zone of the body wall covered by the flexible wall of the disk;

pushing the attachment through the needle by dint of said control rod in order to extract one of the bearing surfaces of the attachment outside the needle and to deploy this surface, then retracting the needle in order to extract said tapered intermediate portion and the other bearing surface from the attachment so that said other bearing surface rests against the body wall on the side opposite that against which the disk rests.

13. The surgical process according to claim 12, characterized in that attachments are placed on the whole periphery of the disk, in order to hold said disk against the body wall and to provide permanent occlusion of the hole contained in said wall.

14. The surgical process according to claim 12, characterized in that one or several attachments are inserted on a marginal sector of the periphery of the disk, so that the disk does not occlude permanently the hole to be treated and may operate like a flap.

* * * * *